United States Patent [19]

Rodriguez et al.

[11] 4,221,789

[45] Sep. 9, 1980

[54] LACTAM-N-ACETIC ACIDS AND THEIR AMIDES

[75] Inventors: Ludovic Rodriguez, Brussels; Lucien Marchal, Lillois, both of Belgium

[73] Assignee: UCB, Societe Anonyme, Belgium

[21] Appl. No.: 36,987

[22] Filed: May 7, 1979

[30] Foreign Application Priority Data

May 8, 1978 [GB] United Kingdom ............... 18160/78

[51] Int. Cl.$^2$ ................. A61K 31/395; C07D 207/12; C07D 223/10; C07D 401/06

[52] U.S. Cl. ........................... 424/244; 260/239.3 A; 260/239.3 R; 260/326.36; 260/326.43; 424/248.54; 424/250; 424/267; 424/274; 544/130; 544/141; 544/360; 544/372; 546/188; 546/208; 546/216; 546/243

[58] Field of Search ................... 260/326.43, 239.3 R; 544/141, 372, 130, 360; 546/243, 208, 188; 424/244, 248.54, 250, 267, 274

[56] References Cited

U.S. PATENT DOCUMENTS

| | | | |
|---|---|---|---|
| 2,657,215 | 10/1953 | Shelley | 260/326.43 |
| 3,751,262 | 8/1973 | Ru et al. | 546/243 X |

FOREIGN PATENT DOCUMENTS 1039113  8/1966  United Kingdom .
1309692  3/1973  United Kingdom .

*Primary Examiner*—Dolph H. Torrence

*Attorney, Agent, or Firm*—Wenderoth, Lind & Ponack

[57] ABSTRACT

New lactam-N-acetic acids and amides thereof having the formula

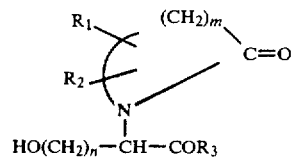

wherein
 $R_1$ and $R_2 =$ H, $C_1$-$C_4$-alkyl, aryl or halogen-substituted aryl,
 $R_3 =$ OH or —NR$_4$R$_5$,
 $R_4$ and $R_5 =$ H, $C_1$-$C_4$-alkyl, cycloalkyl, aralkyl or, taken together with the N atom form alkyleneimino, oxa-alkyleneimino, aza-alkyleneimino or N-benzyl-aza-alkyleneimino,
 m is 3, 4 or 5, preferably 3,
 n is 0, 1 or 2, preferably 2;

and the pharmaceutically acceptable salts of said acids. Processes for producing these compounds and pharmaceutical compositions containing the same are also given. These compounds show amongst others beneficial activity on the mnemic processes and cardiac activity.

18 Claims, No Drawings

LACTAM-N-ACETIC ACIDS AND THEIR AMIDES

The present invention relates to new alpha-hydroxy- or alpha-(hydroxyalkyl)-lactam-N-acetic acids, to the pharmaceutically acceptable salts thereof, to their amides as well as to processes for the preparation thereof. It relates also to pharmaceutical compositions containing these compounds.

British Patent Specification No. 1,039,113 discloses amides of lactam-N-acetic acids, the most representative of which, with respect to its therapeutic properties, is piracetam or 2-oxo-1-pyrrolidineacetamide, called hereinafter compound A.

British Patent Specification No. 1,309,692 discloses amides of alpha-alkyl-lactam-N-acetic acids; a typical representative thereof is alpha-ethyl-2-oxo-1-pyrrolidineacetamide, called hereinafter compound B.

These compounds have interesting therapeutic properties, in particular because of their activity on the central nervous system and more especially on the mnemic processes.

Further, lactam-N-acetic acids are also known, in particular 2-oxo-1-pyrrolidineacetic acid (Ber.40,(1907),2840–41), called hereinafter compound C. As far as is known, however, it has not been shown that these acids possess therapeutic properties.

We have now found that on introducing a hydroxyl group in the alpha-position of the lactam-N-acetic acids or their amides or on the lateral alkyl chain of the alpha-alkyl-lactam-N-acetic acids or their amides, new compounds are obtained which possess the valuable therapeutic properties of the compounds disclosed in the above-mentioned Patent Specifications, but at much lower active doses. Thus, these new compounds show a superior activity on the mnemic processes than the corresponding amides of the lactam-N-acetic acids, in particular the compounds A and B mentioned above. Moreover, we have found that these new compounds have an appreciable cardiac activity.

Thus, the present invention provides new compounds having the formula

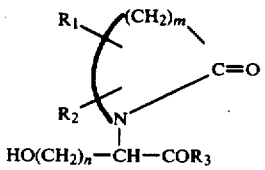

(I)

wherein
R₁ and R₂ independently represents a hydrogen atom, a straight or branched chain alkyl radical containing 1 to 4 carbon atoms, an unsubstituted aryl radical or an aryl radical being substituted by halogen,
R₃ is a hydroxyl group or an —NR₄R₅ group, wherein each of R₄ and R₅, taken separately, represents a hydrogen atom, a straight or branched chain alkyl radical containing 1 to 4 carbon atoms, a cycloalkyl or an aralkyl radical, or R₄ and R₅, taken together with the nitrogen atom to which they are attached, form a heterocyclic radical containing at most 7 ring members, selected from the group consisting of alkyleneimino, oxa-alkyleneimino, aza-alkyleneimino and N-benzyl-aza-alkyleneimino radicals,
m is 3, 4 or 5, preferably 3 and
n is 0, 1 or 2, preferably 2.

When m is 3, 4 or 5, the compounds of formula I are respectively derivatives of 2-pyrrolidinone, 2-piperidinone or hexahydro-2H-azepin-2-one.

As preferred examples of alkyl radicals, there may be mentioned the methyl, ethyl, propyl, isopropyl and butyl radicals.

As preferred example of aryl radicals, there may be mentioned the phenyl radical.

As preferred examples of cycloalkyl radicals, there may be mentioned the cyclopentyl and cyclohexyl radicals.

As preferred example of aralkyl radicals, there may be mentioned the benzyl radical.

The alkyleneimino radical is preferably piperidino, the oxa-alkyleneimino radical is preferably morpholino and the aza-alkyleneimino radical is preferably piperazino.

The preferred compounds of the invention are:
alpha-hydroxy-2-oxo-1-pyrrolidineacetic acid;
alpha-(2-hydroxyethyl)-2-oxo-1-pyrrolidineacetamide;
4-[4-hydroxy-2-(2-oxo-1-pyrrolidinyl)butyryl]-morpholine;
N,N-diethyl-alpha-(2-hydroxyethyl)-2-oxo-1-pyrrolidineacetamide;
N-cyclopentyl-alpha-(2-hydroxyethyl)-2-oxo-1-pyrrolidineacetamide;
N-benzyl-alpha-(2-hydroxyethyl)-2-oxo-1-pyrrolidineacetamide.

The compounds of formula I have valuable pharmaceutical properties. In particular, they have a beneficial activity on the mnemic processes and a protective activity against hypoxic type aggressions. Thus, their first use is in geropsychiatry, a field in which disorders of the memory occur due not only to senile cellular alterations but also to a decrease in the supply of oxygen to the brain as a result of isolated or repeated vascular accidents. Furthermore, the compounds of formula I are useful in numerous other clinical fields, such as the prevention and treatment of cerebrovascular accidents and cardiovascular deficiencies, post-traumatic or toxic comas, memory disorders, difficulties of mental concentration and the like.

The compounds of formula I, in which n is 1 or 2 and R₃ is a hydroxyl group, can be prepared by reacting, in an inert solvent, an alkali metal derivative of a lactam of the formula

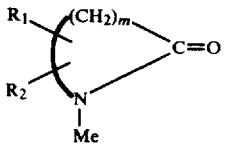

(II)

wherein R₁, R₂ and m have the meanings given above and Me is an alkali metal, with an alpha-bromolactone of the formula

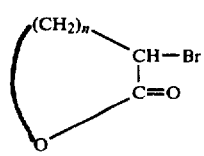

(III)

wherein n has the meaning given above, whereafter the resulting lactone of an alpha-(hydroxyalkyl)-lactam-N-acetic acid of the formula

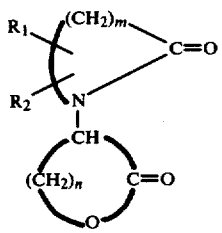
(IV)

wherein $R_1$, $R_2$, m and n have the meanings given above, is subjected to hydrolysis by means of an alkali metal hydroxide, and finally liberating the free acid by acidification from the resulting alkali metal salt of an alpha-(hydroxyalkyl)-lactam-N-acetic acid of the formula

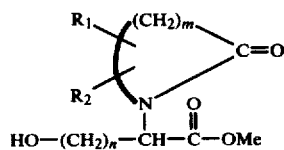
(V)

wherein $R_1$, $R_2$, m and n have the meanings given above and Me represents an alkali metal.

In order to prepare compounds of formula I, in which n is 1 or 2 and $R_3$ is an $-NR_4R_5$ group, a lactone of an alpha-(hydroxyalkyl)-lactam-N-acetic acid of formula IV is first synthesized as described above, whereafter the said lactone is reacted with a nitrogen compound of the formula

(VI), wherein $R_4$ and $R_5$ have the meanings given above.

In the particular case of the preparation of compounds of formula I, in which n is 0 and $R_3$ is a hydroxyl group, glyoxylic acid is reacted with a lactam of the formula

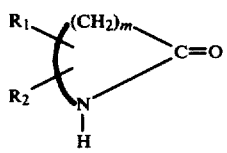
(VII)

wherein $R_1$, $R_2$ and m have the meanings given above.

Finally, in order to prepare compounds of formula I, in which n is 0 and $R_3$ is an $-NR_4R_5$ group, glyoxylic acid or an ester thereof is first reacted with a lactam of formula VII, whereafter the resulting alpha-hydroxy-lactam-N-acetic acid of the formula

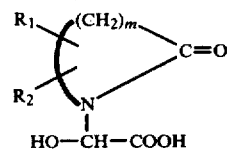
(VIII)

wherein $R_1$, $R_2$ and m have the meanings given above, or the corresponding ester, is condensed with a nitrogen compound of the formula

(VI), wherein $R_4$ and $R_5$ have the meanings given above. However, if the nitrogen compound of formula VI is condensed with the alpha-hydroxy-lactam-N-acetic acid of formula VIII, the said acid should first be activated, in known manner, by means of a conventional reagent, such as for example dicyclohexylcarbodiimide.

The present invention also relates to the pharmaceutically acceptable salts of the lactam-N-acetic acids of formula I. As examples of such salts, there may be mentioned the metal salts, ammonium salts, salts of organic bases (such as salts of amines, for example dicyclohexylamine) and salts of amino acids.

These salts are obtained by known methods currently used for the preparation of such compounds.

The following examples are given for the purpose of illustrating the present invention. In these examples, the position of the peaks in infrared spectroscopy is given in $cm^{-1}$, while in NMR spectroscopy the chemical shifts are indicated in δ(ppm) as referred to tetramethylsilane (TMS), at 60 MHz.

EXAMPLE 1

Preparation of the intermediate lactones of formula IV 1.1 1-(Tetrahydro-2-oxo-3-furyl)-2-pyrrolidinone 60.5 g (1.265 mol) of sodium hydride (50% commercial suspension in paraffin, previously washed twice with benzene) are suspended in 575 ml of anhydrous benzene and 98 g (1.15 mol) of 2-pyrrolidinone are added dropwise to the suspension. The mixture is then heated under reflux until no more gas is evolved. A solution of 237 g (1.44 mol) of 3-bromodihydro-2(3H)-furanone in 60 ml of anhydrous benzene is then added dropwise, while keeping the temperature at 40° to 50° C. After completion of the addition, the reaction mixture is further heated for 1 hour under reflux. It is then cooled and the sodium bromide formed is filtered off. The benzene solution is evaporated under reduced pressure and the residue distilled at 162°–164° C./0.001 mbar, the distillate obtained being in the form of a syrup which crystallizes rapidly. 100.8 g (yield: 52% of theory) of 1-(tetrahydro-2-oxo-3-furyl)-2-pyrrolidinone are obtained. M.P.: 80°–81° C.

Analysis for $C_8H_{11}NO_3$ (M.W. 169) in %: Calculated: C 56.80; H 6.51; N 8.28. Found: C 56.70; H 6.58; N 8.25.

IR spectrum (KBr): 1785, 1770 (CO 2-oxo-furyl); 1690 (CO pyrrolidinone).

1.2

3-Methyl-1-(tetrahydro-2-oxo-3-furyl)-2-pyrrolidinone

Prepared similarly to 1.1 except that the starting material is 3-methyl-2-pyrrolidinone and the reaction mixture is heated under reflux for 16 hours. The product obtained distils at 140°–150° C./0.006 mbar; yield: 8.2 g (22% of theory). The product is in the form of a syrup.

IR spectrum (film): 1775 (CO 2-oxo-furyl); 1680 (CO pyrrolidinone).

1.3
3-n-Butyl-1-(tetrahydro-2-oxo-3-furyl)-2-pyrrolidinone

Prepared similarly to 1.1 except that the starting material is 3-n-butyl-2-pyrrolidinone and the residue obtained after evaporation of the solvent is used without purification for the preparation of the compound of Example 4.4. Yield: 71% of theory (crude product).

The following compounds are prepared in the same manner:

1.4
4-p-Chlorophenyl-3-phenyl-1-(tetrahydro-2-oxo-3-furyl)-2-pyrrolidinone

Yield: almost 100% of theory.

IR spectrum (film): 1775 (CO 2-oxo-furyl); 1680 (CO pyrrolidinone); 825 (para-substituted phenyl); 700, 750 (phenyl).

1.5
3,5-Dimethyl-1-(tetrahydro-2-oxo-3-furyl)-2-pyrrolidinone

Yield: about 10% of theory.

IR spectrum (film): 1770 (CO 2-oxo-furyl); 1670 (CO pyrrolidinone).

1.6 1-(Tetrahydro-2-oxo-3-furyl)-2-piperidinone 1.25 g (0.05 mol) of sodium hydride (2.5 g of a 50% commercial suspension in paraffin, previously washed twice with benzene) are suspended in 50 ml of anhydrous N,N-dimethylformamide. A solution of 4.95 g (0.05 mol) of 2-piperidinone in 20 ml of N,N-dimethylformamide is added dropwise to the suspension. The mixture is then heated to 60° C. until no more gas is evolved, whereafter it is cooled. A solution of 8.25 g (0.05 mol) of 3-bromodihydro-2(3H)-furanone in 20 ml of anhydrous N,N-dimethylformamide is added dropwise while keeping the temperature at 5° to 10° C. The mixture is then stirred at 60° C. for 5 hours. N,N-Dimethylformamide is evaporated off under reduced pressure. The residue is taken up in chloroform and the insoluble matter filtered off on Norit. The filtrate is again evaporated and 9.8 g of a heavy syrup are obtained. Mass spectrum: M+· at 183 m/e.

The product is used in this form in Example 4.6 for the preparation of alpha-(2-hydroxyethyl)-2-oxo-1-piperidineacetamide.

EXAMPLE 2

Preparation of an alpha-hydroxy-lactam-N-acetic acid of formula I (n=0; $R_3$=OH)

alpha-Hydroxy-2-oxo-1-pyrrolidineacetic acid (dicyclohexylamine salt)

8.5 g (0.1 mol) of 2-pyrrolidinone are added to 9.2 g (0.1 mol) of glyoxylic acid monohydrate, the temperature rising spontaneously to 35° C. On completion of the addition, the reaction mixture is heated for 15 minutes at 100° C. The temperature is then lowered to 50° C. and 15 ml of carbon tetrachloride are added thereto, followed by 10 ml of diethyl ether. The reaction mixture separates into two phases. The lower carbon tetrachloride phase is separated by decantation, washed twice with diethyl ether and then evaporated in vacuo. The residue (18 g) is taken up in absolute ethanol and 18 ml of dicyclohexylamine are added to the solution. The dicyclohexylamine salt which precipitates is recrystallized from ethanol containing a little diethyl ether, thus giving 17.7 g of the dicyclohexylamine salt of alphahydroxy-2-oxo-1-pyrrolidineacetic acid. M.P.: 139°–140° C.; yield: 52% of theory.

Analysis for $C_{18}H_{32}N_2O_4$ (M.W. 340) in %: Calculated: C 63.58; H 9.4; N 8.24. Found: C 63.6; H 9.4; N 8.27.

IR spectrum (KBr): 3400 (OH); 1675 (CO pyrrolidinone); 1620 (COO−).

Mass spectrum: M+· (acid) non-existent, but M+·—COOH present at 114 m/e; M+· (dicyclohexylamine) at 181 m/e.

NMR spectrum (CDCl$_3$):

| 1.0 to 3.2 | multiplet | 28 H | (two cyclohexyl + 6H pyrrolidinone) |
|---|---|---|---|
| 5.54 | singlet | 1 H | $H^\alpha$ |
| 8 to 9 | broad | 3 H | OH/COOH/NH |

EXAMPLE 3

Preparation of an alpha-(hydroxyalkyl)-lactam-N-acetic acid of formula I (n=2; $R_3$=OH)

alpha-(2-Hydroxyethyl)-2-oxo-1-pyrrolidineacetic acid 67.6 g (0.4 mol) of 1-(tetrahydro-2-oxo-3-furyl)-2-pyrrolidinone and 32 g (0.8 mol) of sodium hydroxide in 210 ml of water are heated for 2 hours under reflux, cooled and then acidified with hydrochloric acid to a pH value of 1. The reaction mixture is evaporated to dryness under reduced pressure and the residue taken up three times in benzene and evaporated in vacuo. The residue obtained is finally treated with a mixture of chloroform and ethanol (4:1 v/v) and the insoluble material filtered off. The filtrate is evaporated and the residue is recrystallized from ethanol. 22.7 g (yield: 30% of theory) of alpha-(2-hydroxyethyl)-2-oxo-1-pyrrolidineacetic acid are obtained. M.P.: 123°–124° C.

Analysis for $C_8H_{13}NO_4$ (M.W. 187) in %: Calculated: C 51.38; H 6.95; N 7.48. Found: C 51.30; H 6.90; N 7.39.

NMR spectrum (DMSO):

| 2.15 | multiplet | 6 H | 4 $H^3$ + $^4$ pyrrolidinone + 2 $H^1$ ethyl |
|---|---|---|---|
| 3.37 | multiplet | 4 H | 2 $H^5$ pyrrolidinone + 2 $H^2$ ethyl |
| 4.62 | quartet | 1 H | $H^\alpha$ |
| 8.50 | broad | 2 H | OH and COOH |

EXAMPLES 4 TO 6

Preparation of amides of alpha-(hydroxyalkyl)-lactam-N-acetic acids of formula I (n=2; $R_3$=—$NR_4R_5$)

4.1
alpha-(2-Hydroxyethyl)-2-oxo-1-pyrrolidineacetamide 10.15 g (0.06 mol) of 1-(tetrahydro-2-oxo-3-furyl)-2-pyrrolidinone are dissolved in 100 ml of methanol and the solution is saturated with ammonia, the temperature rising spontaneously to 40° C. The mixture is kept at that temperature for 30 minutes, whereupon it is allowed to return to ambient temperature. The reaction mixture is then evaporated under reduced pressure and the resulting powder is recrystallized from absolute ethanol. 10 g of alpha-(2-hydroxyethyl)-2-oxo-1-pyrrolidineacetamide are obtained. M.P.: 164°–165° C.; yield: 90% of theory.

Analysis for $C_8H_{14}N_2O_3$ (M.W. 186) in %: Calculated: C 51.65; H 7.58; N 15.05. Found: C 51.70; H 7.60; N 14.86.

IR spectrum (KBr): 3340, 3180 ($NH_2$); 1695 (CO pyrrolidinone); 1650 (CO amide); 1075 (OH).

NMR spectrum (DMSO):

| 2.15 | multiplet | 6 H | 4 $H^{3+4}$ pyrrolidinone + 2 $H^1$ ethyl |
|---|---|---|---|
| 3.40 | multiplet | 4 H | 2 $H^5$ pyrrolidinone + 2 $H^2$ ethyl |
| 4.46 | multiplet | 2 H | OH + $H^\alpha$ |
| 7.08 to 7.30 | broad | 2 H | $CONH_2$ |

The following compounds 4.2 to 4.6 are obtained by the same method:

4.2
alpha-(2-Hydroxyethyl)-3-methyl-2-oxo-1-pyrrolidineacetamide

M.P.: 101°–102° C.; yield: 86% of theory.

Analysis for $C_9H_{16}N_2O_3$ (M.W. 200) in %; Calculated: C 54.0; H 8.0; N 14.0. Found: C 53.71; H 7.95; N 13.92.

IR spectrum (KBr): 3470 (OH); 3310, 3160 ($NH_2$); 1695 (CO pyrrolidinone); 1640 ($CONH_2$); 1055 (OH).

NMR spectrum (DMSO):

| 1.05 | doublet | 3 H | $CH_3$ |
|---|---|---|---|
| 1.25–2.35 | multiplet | 5 H | 3 $H^{3+4}$ pyrrolidinone + 2 $H^1$ ethyl |
| 3.35 | multiplet | 4 H | 2 $H^5$ pyrrolidinone + 2 $H^2$ ethyl |
| 4.45 | multiplet | 2 H | OH + $H^\alpha$ |
| 7.15 | doublet | 2 H | $CONH_2$ |

Mass spectrum: $M^{+\cdot}$ at 200 m/e.

4.3
alpha-(2-Hydroxyethyl)-3,5-dimethyl-2-oxo-1-pyrrolidineacetamide

Syrup; yield: 51% of theory.

Analysis for $C_{10}H_{18}N_2O_3$ (M.W. 214) in %: Calculated: C 56.07; H 8.41; N 13.08. Found: C 55.5; H 8.5; N 12.92.

IR spectrum (CHCl$_3$): 3470 (OH); 3360, 3180 ($NH_2$); 1660 to 1690 (CO); 1050 (OH).

NMR spectrum (CDCl$_3$):

| 1.21 | multiplet | 6 H | 2 $CH_3$ |
|---|---|---|---|
| 1.6 to 2.9 | multiplet | 5 H | 3 $H^{3+4}$ pyrrolidinone + 2 $H^1$ ethyl |
| 3.6 | multiplet | 4 H | $H^5$ pyrrolidinone + 2 $H^2$ ethyl + OH |
| 4.30 | quartet | 1 H | $H^\alpha$ |
| 6.20 to 7.30 | broad | 2 H | $CONH_2$ |

Mass spectrum: $M^{+\cdot}$ at 214 m/e.

4.4
3-n-Butyl-alpha-(2-hydroxyethyl)-2-oxo-1-pyrrolidineacetamide

M.P.: 90°–91° C.; yield: 26% of theory.

Analysis for $C_{12}H_{22}N_2O_3$ (M.W. 242) in %: Calculated: C 59.5; H 9.09; N 11.57. Found: C 59.67; H 9.20; N 11.54.

IR spectrum (KBr): 3390, 3340, 3180 (OH, $NH_2$); 1710 (CO pyrrolidinone); 1660 ($CONH_2$); 1050 (OH).

NMR spectrum (CDCl$_3$):

| 0.7 to 2.5 | multiplet | 13 H | $C_4H$ + 2 $H^4$ pyrrolidinone + 2 $H^1$ ethyl |
|---|---|---|---|
| 3.2 to 4.0 | multiplet | 6 H | 3 $H^{3+5}$ pyrrolidinone + 2 $H^2$ ethyl + CH |
| 4.86 | triplet | 1 H | $H^\alpha$ |
| 6.20 and 7.05 | doublet | 2 H | $CONH_2$ |

Mass spectrum: $M^{+\cdot}$ at 242 m/e.

4.5
4-p-Chlorophenyl-alpha-(2-hydroxyethyl)-3-phenyl-2-oxo-1-pyrrolidineacetamide M.P.: 60°–61° C.; yield: 23% of theory.

Analysis for $C_{20}H_{21}ClN_2O_3$ (M.W. 372.5) in %: Calculated: C 64.43; H 5.64; N 7.52. Found: C 63.39; H 5.50; N 7.64.

IR spectrum (KBr): 3360, 3200 (OH, $NH_2$); 1670 (broad CO); 1050 (OH); 820 (p-chlorophenyl); 700, 750 (phenyl).

NMR spectrum (CDCl$_3$):

| 2.0 | broad | 2 H | 2 $H^1$ ethyl |
|---|---|---|---|
| 3.30 to 4.10 | multiplet | 6 H | 4 $H^{3+4+5}$ pyrrolidinone + 2 $H^2$ ethyl |
| 5.0 | triplet | 1 H | $H^\alpha$ |
| 5.85 | broad | 1 H | OH |
| 7.15 | multiplet | 11 H | 9 H two phenyls + $CONH_2$ |

Mass spectrum: $M^{+\cdot}$ at 372 m/e.

4.6
alpha-(2-Hydroxyethyl)-2-oxo-1-piperidineacetamide

The resins obtained after evaporation of the reaction mixture are chromatographed on a silica column (eluent: 95:5 chloroform-methanol mixture). A slightly colored powder is thus obtained.

IR spectrum (KBr): 3430 (OH); 3180 to 3270 ($NH_2$); 1695 (CO piperidinone); 1615 ($CONH_2$).

NMR spectrum (CDCl$_3$):

| 1.5 to 2.7 | multiplet | 8 H | 6 $H^{3+4+5}$ piperidinone + 2 $H^1$ ethyl |
|---|---|---|---|
| 2.9 to 4.0 | multiplet | 5 H | 2 $H^6$ piperidinone + 2 $H^2$ ethyl + OH |
| 5.3 | multiplet | 1 H | H α |
| 6.3 to 6.92 | doublet | 2 H | $CONH_2$ |

Mass spectrum: $M^{+\cdot}$ at 200 m/e.

5.1
N-n-Butyl-alpha-(2-hydroxyethyl)-2-oxo-1-pyrrolidineacetamide 10.14 g (0.06 mol) of 1-(tetrahydro-2-oxo-3-furyl)-2-pyrrolidinone are dissolved in 50 ml of methanol and 8.78 g (0.12 mol) of n-butylamine are added to the solution. The reaction mixture is heated under reflux (65° C.) for 3 hours and then evaporated under a high vacuum. 12.3 g (yield: 85% of theory) of N-n-butyl-alpha-(2-hydroxyethyl)-2-oxo-1-pyrrolidineacetamide are obtained in the form of a syrup.

Analysis for $C_{12}H_{22}N_2O_3$ (M.W. 242) in %: Calculated: C 59.5; H 9.09; N 11.6. Found: C 59.32; H 9.09; N 11.54.

IR spectrum (film): 3440 (OH); 3300 (NH); 1690 to 1640 (CO); 1540 (NH); 1055 (OH).

NMR spectrum (CDCl$_3$):

| | | | |
|---|---|---|---|
| 0.8 to 2.8 | multiplet | 13 H | |
| 3.0 to 4.0 | multiplet | 7 H | 2 H$^5$ pyrrolidinone + N—CH$_2$ (butyl) + 2 H$^2$ ethyl + OH |
| 4.88 | triplet | 1 H | H$^\alpha$ |
| 7.15 | triplet | 1 H | NH |

Mass spectrum: M+ at 242 m/e.

The following compounds 5.2 to 5.4 are prepared in a similar manner:

5.2
N-Cyclohexyl-alpha-(2-hydroxyethyl)-2-oxo-1-pyrrolidineacetamide

M.P.: 122°–123° C.; yield: 73% of theory.

Analysis for C$_{14}$H$_{24}$N$_2$O$_3$ (M.W. 268) in %: Calculated: C 62.7; H 8.95; N 10.44. Found: C 62.52; H 8.94; N 10.42.

IR spectrum (KBr): 3500 (OH); 3300 (NH); 1660 (CO); 1530 (NH); 1050 (OH).

NMR spectrum (CDCl$_3$):

| | | | |
|---|---|---|---|
| 1.9 to 2.8 | multiplet | 16 H | 4 H$^{3+4}$ pyrrolidinone + 2 H$^1$ ethyl + 10 H of the CH$_2$ of cyclohexyl |
| 3.0 to 4.0 | multiplet | 6 H | 2 H$^5$ pyrrolidinone + 2 H$^2$ ethyl + CH of cyclohexyl + OH |
| 4.85 | triplet | 1 H | H$^\alpha$ |
| 6.98 | doublet | 1 H | NH |

Mass spectrum: M+ at 268 m/e.

5.3
N,N-Diethyl-alpha-(2-hydroxyethyl)-2-oxo-1-pyrrolidineacetamide

Syrup; yield: 33% of theory.

Infrared spectrum (film): 3420 (OH); 1660 (CO pyrrolidinone); 1635 (CO amide); 1055 (OH).

NMR spectrum (CDCl$_3$):

| | | | |
|---|---|---|---|
| 1.1 to 1.18 | 2 triplets | 6 H | 2 CH$_3$ (diethyl) |
| 1.7 to 2.6 | multiplet | 6 H | 4 H$^{3+4}$ pyrrolidinone + 2 H$^1$ ethyl |
| 3.1 to 3.8 | multiplet | 9 H | 2 CH$_2$ (diethyl) + 2 H$^5$ pyrrolidinone + 2 H$^2$ ethyl + OH |
| 5.18 | triplet | 1 H | H$^\alpha$ |

Mass spectrum: M+ at 242 m/e.

5.4
alpha-(2-Hydroxyethyl)-N-isopropyl-2-oxo-1-pyrrolidineacetamide

Syrup; yield: 83% of theory.

Analysis for C$_{11}$H$_{20}$N$_2$O$_3$ (M.W. 228) in %: Calculated: C 57.89; H 8.17; N 12.28. Found: C 55.08; H 8.38; N 12.76.

IR spectrum (film): 3420 (OH); 3300 (NH); 1660 to 1690 (CO); 1540 (NH); 1055 (OH).

NMR spectrum (CDCl$_3$):

| | | | |
|---|---|---|---|
| 1.2 | doublet | 6 H | 2 CH$_3$ (isopropyl) |
| | multiplet | 6 H | 4 H$^{3+4}$ pyrrolidinone + 2 H$^1$ ethyl |
| | multiplet | 6 H | 2 H$^5$ pyrrolidinone + 2 H$^2$ ethyl + CH (isopropyl) + OH |
| | triplet | 1 H | H$^\alpha$ |
| 7.0 | doublet | 1 H | NH |

Mass spectrum: M+ at 228 m/e.

6.1
4-[4-Hydroxy-2-(2-oxo-1-pyrrolidinyl)butyryl]-morpholine.

5.07 g (0.03 mol) of 1-(tetrahydro-2-oxo-3-furyl)-2-pyrrolidinone are mixed with 10.45 g (0.12 mol) of morpholine and the reaction mixture is heated at 110° C. for 5 hours. Upon cooling, the product crystallizes. The product is filtered and recrystallized from diethyl ether. 6.3 g (yield: 82% of theory) of 4-[4-hydroxy-2-(2-oxo-1-pyrrolidinyl)butyryl]-morpholine are obtained. M.P.: 105°–106° C.

Analysis for C$_{12}$H$_{20}$N$_2$O$_4$ (M.W. 256) in %: Calculated: C 56.25; H 7.8; N 10.93. Found: C 56.15; H 7.82; N 10.90.

IR spectrum (KBr): 3450 (OH); 1680 (CO pyrrolidinone); 1650 (CO amide); 1050 (OH).

NMR spectrum (CDCl$_3$):

| | | | |
|---|---|---|---|
| 1.8 to 2.6 | multiplet | 6 H | 4 H$^{3+4}$ pyrrolidinone + 2 H$^3$ butyryl |
| 3 to 4 | multiplet | 13 H | 2 H$^5$ pyrrolidinone + 8 H morpholine + 2 H$^4$ butyryl + OH |
| 5.2 | triplet | 1 H | H$^2$ butyryl |

Mass spectrum: M+ at 256 m/e.

The following compounds 6.2 to 6.6 are prepared in a similar manner:

6.2
1-[4-Hydroxy-2-(2-oxo-1-pyrrolidinyl)butyryl]-piperidine

M.P.: 129° C.; yield: 89% of theory.

Analysis for C$_{13}$H$_{22}$N$_2$O$_3$ (M.W. 254) in %: Calculated: C 61.4; H 8.66; N 11.02. Found: C 61.21; H 8.59; N 11.0.

IR spectrum (KBr): 3420 (OH); 1680 (CO pyrrolidinone); 1625 (CO amide); 1055 (OH).

NMR spectrum (CDCl$_3$):

| | | | |
|---|---|---|---|
| 1.3 to 2.7 | multiplet | 12 H | 4 H$^{3+4}$ pyrrolidinone + 6 H piperidine + 2 H$^3$ butyryl |
| 3.2 to 4.0 | multiplet | 9 H | 2 H$^5$ pyrrolidinone + 4 H piperidine + 2 H$^4$ butyryl + OH |
| 5.2 | triplet | 1 H | H$^2$ butyryl |

Mass spectrum: M+ at 254 m/e.

6.3
alpha-(2-Hydroxyethyl)-N-propyl-2-oxo-1-pyrrolidineacetamide

Syrup; yield: 98% of theory.

Analysis for C$_{11}$H$_{20}$N$_2$O$_3$ (M.W. 228) in %: Calculated: C 57.89; H 8.77; N 12.28. Found: C 56.96; H 8.60; N 12.46.

IR spectrum (film): 3420 (OH); 3300 (NH); 1650–1690 (CO); 1535 (NH); 1055 (OH).

NMR spectrum (CDCl$_3$):

| | | | |
|---|---|---|---|
| 0.92 | triplet | 3 H | CH$_3$ (propyl) |
| 1.2 to 2.7 | multiplet | 8 H | 4 H$^{3+4}$ pyrrolidinone + CH$_2$ (propyl) + 2 H$^1$ ethyl |

-continued

| | | | |
|---|---|---|---|
| 3.0 to 4.1 | multiplet | 7 H | 2 H$^5$ pyrrolidinone + CH$_2$ (propyl) + 2 H$^2$ ethyl + OH |
| 4.9 | triplet | 1 H | H$^\alpha$ |
| 7.20 | triplet | 1 H | NH |

Mass spectrum: M+· at 228 m/e.

6.4
1-Benzyl-4-[4-hydroxy-2-(2-oxo-1-pyrrolidinyl)-butyryl]-piperazine.

Syrup; yield: 67% of theory.
IR spectrum (film): 3420 (OH); 1640 to 1690 (CO); 1055 (OH); 745, 700 (phenyl).
NMR spectrum (CDCl$_3$):

| | | | |
|---|---|---|---|
| 1.6 to 3.8 | multiplet | 21 H | |
| 5.18 | triplet | 1 H | H$^2$ butyryl |
| 7.28 | singlet | 5 H | 5 H phenyl |

Mass spectrum: M+· at 345 m/e.

6.5
N-cyclopentyl-alpha-(2-hydroxyethyl)-2-oxo-1-pyrrolidineacetamide

The syrup obtained after evaporation of the reaction mixture under reduced pressure is purified by chromatography on a silica column (eluent: 95:5 chloroform-methanol mixture).

The suitable fractions are joined together, evaporated and the residual syrup is triturated in diethyl ether containing a few drops of chloroform. N-cyclopentyl-alpha-(2-hydroxyethyl)-2-oxo-1-pyrrolidineacetamide crystallizes out. M.P.: 81°-83° C.; yield: 72% of theory.

Analysis for C$_{13}$H$_{22}$N$_2$O$_3$ (M.W.=254) in %: Calculated: C 61.41; H 8.66; N 11.02. Found: C 61.44; H 8.66; N 10.98.

IR spectrum (KBr): 3450 (OH); 3260 (NH); 1680 (CO pyrrolidinone); 1650 (CO amide); 1550 (NH amide); 1060 (OH).

NMR spectrum (CDCl$_3$):

| | | | |
|---|---|---|---|
| 1.6 to 2.8 | multiplet | 14 H | 8 H of the CH$_2$ of cyclopentyl + 4 H$^{3+4}$ pyrrolidinone + 2 H$^1$ ethyl |
| 3.3 to 4.4 | multiplet | 6 H | 2 H$^5$ pyrrolidinone + 2 H$^2$ ethyl + OH + CH of cyclopentyl |
| 4.85 | triplet | 1 H | H$^\alpha$ |
| 7.20 | doublet | 1 H | NH |

Mass spectrum: M+· at 254 m/e.

6.6
N-Benzyl-alpha-(2-hydroxyethyl)-2-oxo-1-pyrrolidineacetamide

The syrup obtained after evaporation of the reaction mixture crystallizes very slowly. The crystals are washed with diethyl ether. M.P.: 90°-92° C.; yield: 71% of theory.

Analysis for C$_{15}$H$_{20}$N$_2$O$_3$ (M.W. 276) in %:
Calculated: C 65.21; H 7.24; N 10.14. Found: C 65.02; H 7.34; N 10.23.

IR spectrum (film): 3400 (OH); 3300 (NH); 1640 to 1690 (CO); 1540 (NH); 1065 (OH); 710 (phenyl).
NMR spectrum (CDCl$_3$):

| | | | |
|---|---|---|---|
| 1.7 to 2.5 | multiplet | 6 H | 4 H$^{3+4}$ pyrrolidinone + 2 H$^1$ ethyl |
| 3.2 to 3.9 | multiplet + triplet | 5 H | 2 H$^3$ pyrrolidinone + 2 H$^2$ ethyl + OH |
| 4.4 | doublet | 2 H | CH$_2$ (benzyl) |
| 4.9 | triplet | 1 H | H$^\alpha$ |
| 7.23 | singlet | 5 H | 5 H phenyl |
| 7.6 | triplet | 1 H | NH |

Mass spectrum: M+· at 276 m/e.

Pharmacological Tests

The compounds of formula I were subjected to pharmacological tests, the results of which are given below.

I. Action on Mnemic Processes (A) The action on mnemic processes is first shown by the ability of the compounds to improve a type of memory retention in the rat. The principle of the active avoidance test (see M. GREINDL and S. PREAT, Arch. Int. Pharmacodyn. Therap. 223, (1976), (1), 168-171) developed in our laboratories and used for this purpose, may be described as follows: the withdrawal reaction of a rat's paw when subjected to an increasing, quantified pressure is observed. The pressure at which the withdrawal reaction is produced, is called the reaction threshold. This threshold is expressed by the number of graduations of the scale of the apparatus used (Analgesymeter Ugo Basile, Milan) and thus corresponds to the minimum pressure which brings about withdrawal when applied to the animal's paw. It is read off directly on the scale of the apparatus used.

When tested 24 hours later, the control animals do not show any apparent retention of the previous test: avoidance takes place at a stimulation intensity comparable to that 24 hours earlier. Inversely, animals treated with a substance having a positive effect on the mnemic processes (such as piracetam) show a significant degree of retention: the stimulus to which the rats react by a reflex of avoidance is statistically lower than that of the control animals. A minimum of 20 rats per test are used (10 treated rats and 10 control rats) and the active dose is defined as the minimum dose lowering the stimulus to below 11 graduations.

Subcutaneous administration of the compounds of formula I gave, under these conditions, the results shown in the following Table:

| Compound of Example | Active dose in mmol/kg. |
|---|---|
| 2 | 0.005 |
| 4.1 | 0.002 |
| 5.3 | 0.0002 |
| 6.1 | 0.0002 |
| 6.3 | 0.0001 |
| 6.4 | 0.001 |
| 6.5 | 0.0002 |
| 6.6 | 0.002 |
| Compound A (comparison) | 0.025 |
| Compound B (comparison) | 0.005 |

Compound C (comparison) is inactive at the dose of 0.1 mmol/kg.

This Table shows that these compounds all display, in this test, an activity which is superior to that of compounds A and B, the action of which on the mnemic processes is well known.

(B) The action on the mnemic processes is also shown by the reduction of the spinal fixation time, a test which has been described in literature (see C. GIURGEA and F. MOURAVIEFF-LESUISSE, Arch.Int.Pharmacodyn.191,(1971,No. 2), 279) as an elementary model of memory and which provides pharmacological reactivity in good correlation with clinical physiopathology. In the rat, after unilateral lesion of the cerebellum, there is a postural asymmetry of the hind paws. This asymmetry may persist, even after spinal section, if the animal has passed a sufficient period of time in this position. This time, which is called the spinal fixation time, is 45 minutes under the experimental conditions applied here.

On the other hand, if spinal section is performed before the expiry of this period of time, for example 35 minutes after the onset of asymmetry, the latter disappears.

No animal treated with placebos retains the asymmetry under these conditions.

Inversely, any product which allows the rats to retain the asymmetry (thus effecting spinal fixation), when the spinal section is performed after 35 minutes, is considered to be active.

Intraperitoneal administration of the compounds of formula I gave, under these conditions, the results indicated in the following Table. By "number of animals" is to be understood the number of animals which responded positively to the test in relation to the number of animals tested at the dose indicated:

| Compound of Example | Active dose mmol/kg | Number of animals |
|---|---|---|
| 2 | 0.1 | 4/7 |
| 3 | 0.1 | 4/7 |
| 4.1 | 0.1 | 3/7 |
| 6.6 | 0.1 | 3/7 |
| Compound A (comparison) | 0.2 | 4/9 |
| Compound B (comparison) | 0.2 | 7/22 |
| Compound C (comparison) | 0.32 | 2/4 |

Therefore, it can be seen that the compounds of formula I have the same activity as the reference compounds, but at a significantly lower dose.

II. Cardiac Activity

The compounds of formula I were found to possess an appreciable cardiac activity; this is shown by the "papillary muscle" test.

The method used is that of M. K. CATTELL and H. GOLD (J.Pharmacol.Exptl. Therap.62, (1938), 116-125). The experiment is carried out on a papillary muscle isolated from the cat's heart and dipped in a physiological salt solution to which the compound to be tested is added.

In this test, the compound of Example 4.1 shows an inotropic activity which is superior to that of caffeine.

Thus, at the dose of 10 μg/kg, the increase of the strength of muscular contraction is respectively 7% for the compound of Example 4.1 and 4% for caffeine.

III. Toxicity

The compounds of formula I have a remarkably low toxicity. For instance, their toxicity, when administered intraperitoneally in mice, is shown in the following Table:

| Compound of Example | mg/kg* |
|---|---|
| 2 | > 102 |
| 3 | >1222 |
| 4.1 | >1116 |
| 4.2 | >1200 |
| 4.3 | >1286 |
| 4.4 | >1452 |
| 4.5 | > 224 |
| 5.1 | >1452 |
| 5.2 | >1608 |
| 5.3 | >1452 |
| 5.4 | >1368 |
| 6.1 | >1536 |
| 6.2 | >1524 |
| 6.3 | >1368 |
| 6.4 | > 345 |
| 6.5 | > 762 |
| 6.6 | = 822 |

*Dose which brings about the death of one animal out of three in Irwin's test (S. IRWIN, Gordon Research Conference on Medicinal Chemistry, Colby Junior College, New London, 1959).

Furthermore, when administered intravenously (i.v.) or orally in the rat, the compounds also have a low toxicity, as indicated in the following Table:

| Compound of Example | Route of administration | LD 50 mg/kg (rat) |
|---|---|---|
| 4.1 | i.v. | > 4000 |
| 4.1 | orally | >10000 |

IV. Posology and Administration

The pharmaceutical compositions of the present invention which can be administered orally are in the form of solid or liquid compositions, for example, in the form of tablets, pills, sugar coated pills, gelatine capsules, solutions, syrups and the like. Similarly, the compositions which can be administered parenterally are the pharmaceutical forms known for this purpose, for example, aqueous or oily solutions, suspensions or emulsions.

For rectal administration, the compositions are generally in the form of suppositories.

Pharmaceutical forms such as injectable solutions, injectable suspensions, tablets, drops and suppositories are prepared by conventional pharmaceutical methods. The compounds of the present invention are mixed with a pharmaceutically acceptable, non-toxic solid or liquid vehicle and optionally with a dispersing agent, a disintegrating agent, a lubricant, a stabilizing agent or the like. Preservatives, sweetening agents, coloring agents and the like may, if desired, be added.

Similarly, the solid or liquid pharmaceutical vehicles used in these compositions are well known. Solid pharmaceutical excipients for the preparation of tablets or capsules include, for example, starch, talc, calcium carbonate, lactose, sucrose, magnesium stearate and the like.

The percentage of active product in the pharmaceutical compositions may vary within very wide limits, depending upon the conditions of use and particularly upon the frequency of administration.

Human posology is of the order of 2 × 250 mg per day but may, if desired, vary from 10 mg to 4 g per day.

By way of example of a pharmaceutical composition, a tablet composition containing a compound of formula I is as follows:

| compound of Example 4.1 | 400 mg |
|---|---|
| starch | 61 mg |
| polyvinylpyrrolidone | 8 mg |
| talc | 26 mg |
| magnesium stearate | 5 mg |

We claim:

1. A lactam-N-acetic acid or an amide thereof having the formula

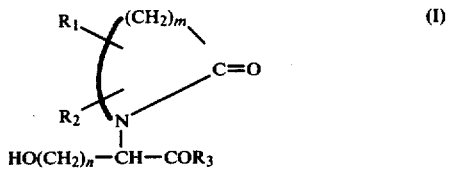

wherein
$R_1$ and $R_2$ independently represents a hydrogen atom, a straight or branched chain alkyl radical containing 1 to 4 carbon atoms, an unsubstituted aryl radical or an aryl radical being substituted by halogen, $R_3$ is a hydroxyl group or an $-NR_4R_5$ group, wherein each of $R_4$ and $R_5$, taken separately, represents a hydrogen atom, a straight or branched chain alkyl radical containing 1 to 4 carbon atoms, a cycloalkyl or an aralkyl radical, or $R_4$ and $R_5$, taken together with the nitrogen atom to which they are attached, form a heterocylic radical containing at most 7 ring members, selected from the group consisting of alkyleneimino, oxa-alkyleneimino, aza-alkyleneimino and N-benzyl-aza-alkyleneimino radicals,
m is 3, 4 or 5 and
n is 0, 1 or 2;
or a pharmaceutically acceptable salt of the said lactam-N-acetic acid.

2. A compound as claimed in claim 1, namely alpha-hydroxy-2-oxo-1-pyrrolidineacetic acid or a pharmaceutically acceptable salt thereof.

3. A compound as claimed in claim 1, namely alpha-(2-hydroxyethyl)-2-oxo-1-pyrrolidineacetic acid or a pharmaceutically acceptable salt thereof.

4. A compound as claimed in claim 1, namely alpha-(2-hydroxyethyl)-2-oxo-1-pyrrolidineacetamide.

5. A compound as claimed in claim 1, namely N,N-diethyl-alpha-(2-hydroxyethyl)-2-oxo-1-pyrrolidineacetamide.

6. A compound as claimed in claim 1, namely 4-[4-hydroxy-2-(2-oxo-1-pyrrolidinyl)butyryl]-morpholine.

7. A compound as claimed in claim 1, namely N-cyclopentyl-alpha-(2-hydroxyethyl)-2-oxo-1-pyrrolidineacetamide.

8. A compound as claimed in claim 1, namely N-benzyl-alpha-(2-hydroxyethyl)-2-oxo-1-pyrrolidineacetamide.

9. A compound as claimed in claim 1, namely alpha-(2-hydroxyethyl)-N-propyl-2-oxo-1-pyrrolidineacetamide.

10. A compound as claimed in claim 1, namely 1-benzyl-4-[4-hydroxy-2-(2-oxo-1-pyrrolidinyl)butyryl]-piperazine.

11. A compound as claimed in claim 1, namely N-cyclohexyl-alpha-(2-hydroxyethyl)-2-oxo-1-pyrrolidineacetamide.

12. The compound as claimed in claim 1 wherein m=3.

13. A process for the preparation of a lactam-N-acetic acid having the formula

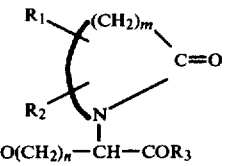

wherein $R_1$ and $R_2$ independently represents a hydrogen atom, a straight or branched chain alkyl radical containing 1 to 4 carbon atoms, an unsubstituted aryl radical or an aryl radical being substituted by halogen, $R_3$ is a hydroxyl group, n is 1 or 2 and m is 3, 4 or 5, which comprises reacting, in an inert solvent, an alkali metal derivative of a lactam of the formula

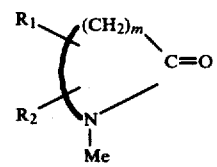

wherein $R_1$, $R_2$ and m have the meanings given above and Me is an alkali metal, with an alpha-bromolactone of the formula

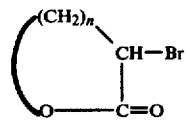

wherein n has the meaning given above, subjecting the resulting lactone of an alpha-(hydroxyalkyl)-lactam-N-acetic acid of the formula

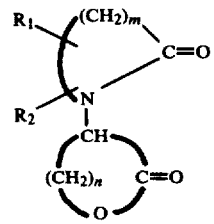

wherein $R_1$, $R_2$, m and n have the meanings given above, to hydrolysis by means of an alkali metal hydroxide, and liberating the free acid by acidification from the resulting alkali metal salt of an alpha-(hydroxyalkyl)-lactam-N-acetic acid of the formula

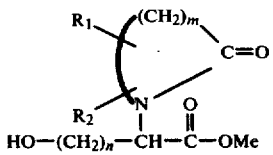

wherein $R_1$, $R_2$, m and n have the meanings given above and Me represents an alkali metal.

14. A process for the preparation of an amide of a lactam-N-acetic acid having the formula

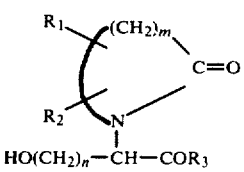

wherein $R_1$ and $R_2$ independently represents a hydrogen atom, a straight or branched chain alkyl radical containing 1 to 4 carbon atoms, an unsubstituted aryl radical or an aryl radical being substituted by halogen, $R_3$ is an $-NR_4R_5$ group wherein each of $R_4$ and $R_5$, taken separately, represents a hydrogen atom, a straight or branched chain alkyl radical containing 1 to 4 carbon atoms, a cycloalkyl or an aralkyl radical, or $R_4$ and $R_5$, taken together with the nitrogen atom to which they are attached, form a heterocyclic radical containing at most 7 ring members, selected from the group consisting of alkyleneimino, oxalkyleneimino, aza-alkyleneimino and N-benzyl-aza-alkyleneimino radicals, n is 1 or 2 and m is 3, 4 or 5, which comprises reacting, in an inert solvent, an alkali metal derivative of a lactam of the formula

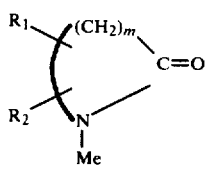

wherein $R_1$, $R_2$ and m have the meanings given above and Me is an alkali metal, with an alpha-bromolactone of the formula

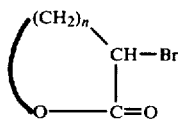

wherein n has the meaning given above, and reacting the resulting lactone of an alpha-(hydroxyalkyl)-lactam-N-acetic acid of the formula

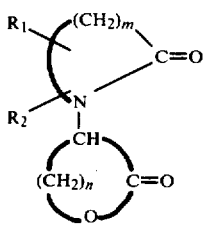

wherein $R_1$, $R_2$, m and n have the meanings given above, with a nitrogen compound of formula

wherein $R_4$ and $R_5$ have the meaning given above.

15. A process for the preparation of a lactam-N-acetic acid having the formula

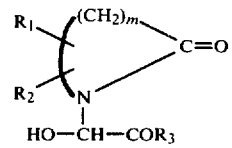

wherein $R_1$ and $R_2$ independently represents a hydrogen atom, a straight or branched chain alkyl radical containing 1 to 4 carbon atoms, an unsubstituted aryl radical or an aryl radical being substituted by halogen, $R_3$ is a hydroxyl group, and m is 3, 4 or 5, which comprises reacting glyoxylic acid with a lactam of the formula

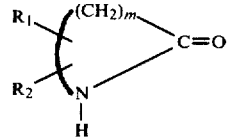

wherein $R_1$, $R_2$ and m have the meanings given above.

16. A process for the preparation of an amide of a lactam-N-acetic acid having the formula

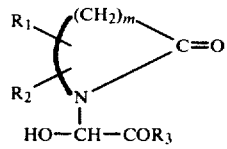

wherein $R_1$ and $R_2$ independently represents a hydrogen atom, a straight or branched chain alkyl radical containing 1 to 4 carbon atoms, an unsubstituted aryl radical or an aryl radical being substituted by halogen, $R_3$ is an $-NR_4R_5$ group wherein each of $R_4$ and $R_5$, taken separately, represents a hydrogen atom, a straight or branched chain alkyl radical containing 1 to 4 carbon atoms, a cycloalkyl or an aralkyl radical, or $R_4$ and $R_5$, taken together with the nitrogen atom to which they are attached, form a heterocyclic radical containing at most 7 ring members, selected from the group consisting of alkyleneimino, oxa-alkyleneimino, aza-alkyleneimino and N-benzyl-aza-alkyleneimino radicals, and m is 3, 4 or 5, which comprises reacting glyoxylic acid or an ester thereof with a lactam of the formula

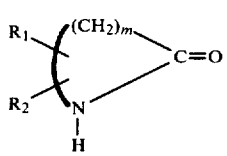

wherein $R_1$, $R_2$ and m have the meanings given above, and condensing the resulting alpha-hydroxyl-lactam-N-acetic acid of the formula

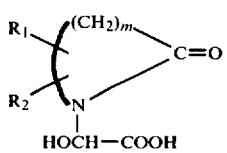

wherein $R_1$, $R_2$ and m have the meanings given above, or the corresponding ester, with a nitrogen compound of the formula

wherein $R_4$ and $R_5$ have the meanings given above.

17. A pharmaceutical composition comprising a therapeutically effective amount of a compound as claimed in claim 1 and a pharmaceutically acceptable solid or liquid diluent or carrier therefor.

18. The composition as claimed in claim 16 wherein m=3.

* * * * *